(12) United States Patent
Nuccitelli et al.

(10) Patent No.: US 8,512,334 B2
(45) Date of Patent: Aug. 20, 2013

(54) NANOSECOND PULSED ELECTRIC FIELD PARAMETERS FOR DESTROYING TUMORS WITH A SINGLE TREATMENT

(75) Inventors: Richard Lee Nuccitelli, Millbrae, CA (US); Pamela Nuccitelli, Millbrae, CA (US); Saleh Sheikh, Hampton, VA (US); Kevin Tran, San Jose, CA (US); Brian Athos, Pleasanton, CA (US); Mark Kreis, San Francisco, CA (US)

(73) Assignee: BioElectroMed Corporation, Burlingame, CA (US)

( * ) Notice: Subject to any disclaimer, the term of this patent is extended or adjusted under 35 U.S.C. 154(b) by 832 days.

(21) Appl. No.: 12/722,441

(22) Filed: Mar. 11, 2010

(65) Prior Publication Data

US 2010/0318082 A1    Dec. 16, 2010

Related U.S. Application Data

(60) Provisional application No. 61/186,798, filed on Jun. 12, 2009.

(51) Int. Cl.
*A61B 18/18* (2006.01)

(52) U.S. Cl.
USPC .................................. 606/41; 606/45

(58) Field of Classification Search
USPC ....................................... 606/32–45
See application file for complete search history.

(56) References Cited

U.S. PATENT DOCUMENTS 8,000,813 B2 * 8/2011 Schoenbach et al. ......... 607/154

* cited by examiner

*Primary Examiner* — Linda Dvorak
*Assistant Examiner* — Amanda Scott
(74) *Attorney, Agent, or Firm* — Kilpatrick Townsend & Stockton LLP

(57) ABSTRACT

Nanosecond pulsed electric field (nsPEF) parameters for destroying tumors with a single treatment are described. A nsPEF generator may be used with an electrode assembly to apply the pulses to one or more tumors where the parameters for the nsPEF are optimized for treating such tumors.

13 Claims, 14 Drawing Sheets

NANOSECOND PULSED ELECTRIC FIELD PARAMETERS FOR DESTROYING TUMORS WITH A SINGLE TREATMENT

CROSS-REFERENCE TO RELATED APPLICATIONS

This application claims the benefit of priority to U.S. Prov. 61/186,798 filed Jun. 12, 2009, which is incorporated herein by reference in its entirety.

FIELD OF THE INVENTION

The present invention relates to methods and apparatus for treating tumors utilizing nanosecond pulsed electric fields (nsPEF). More particularly, the present invention relates to methods and apparatus for destroying tumors with nanosecond pulsed electric fields (nsPEF) which are optimized for treating such tumors.

BACKGROUND OF THE INVENTION

As described in U.S. Pat. No. 6,326,177 (Schoenbach et al.), which is incorporated herein by reference in its entirety, a method for intracellular electro-manipulation is described. The method includes applying at least one ultrashort electric field pulse to target cells where the ultrashort electric field pulse has sufficient amplitude and duration to modify subcellular structures in the target cells and does not exceed the breakdown field of the medium containing the target cells. The amplitude and duration of the ultrashort electric field pulse are typically insufficient to substantially alter permeability of the surface membranes of the target cells, e.g., by irreversibly disrupting the cell surface membranes. An apparatus for intracellular electro-manipulation is also provided. The apparatus includes a pulse generator capable of producing an ultrashort electric pulse output and a delivery system capable of directing the electric pulse output to target cells.

However, such devices and methods are insufficient for facilitating treatment of targeted tissue regions, such as tumors. Such devices may thus require multiple treatments exposing the patient to additional risks.

Accordingly, there exists a need for methods and devices which are efficacious and safe in facilitating the treatment of tumors in patients.

SUMMARY OF THE INVENTION

In delivering nanosecond pulsed electric fields (nsPEF) to a region of tissue, such as a tumor, it is possible to precisely control the number of pulses delivered as well as the frequency of those pulses to deliver electrotherapy via an electrode assembly designed to draw tissue into a recessed cavity in order to immobilize the tissue and position the electrodes firmly against or within the tissue. The recessed cavity may be varied in its size to match a size of any particular tumor to be treated such that the treated tumor may be received within the cavity in close proximity or in direct contact against the electrodes.

The electrode assembly may be configured into a variety of configurations for delivering electrotherapy and may also utilize suction to fix in place the tissue being treated. For example, six (6) spaced apart planar electrodes may be positioned circumferentially about the recessed cavity. In other variations, the electrode assembly may comprise a support member having a pair of "U"-shaped planar electrodes disposed on the periphery of the recessed cavity. Other variations may include a pair of spaced apart parallel plate electrodes while other variations may include a plurality of needle electrodes which are mounted at the base of a back plate to control the penetration depth of the tissue as it is sucked into the recessed cavity.

The back plate of each recessed cavity may have multiple apertures, such as on the order of 100 µm in diameter. An air pump, e.g., an oscillating diaphragm air pump or other suction source, is then coupled to the support member on the side of the base wall support opposite the recessed cavity and is used to generate a mild suction that pulls the tissue to be treated into the cup-like volume.

In use, the support member may suction or draw in tissue to be treated from various regions of the body into the recessed cavity into contact or proximity to the electrodes. Drawing in the tissue may further facilitate tissue treatment by clearly defining the treatment area to be treated for the operator. When nsPEF is applied to a tissue region such as a tumor, if a large resistance between the electrode and the tumor restricts current flow (such as the presence of the stratum corneum in skin), the field may not pass into the tumor effectively. Thus it may be desirable to apply, in one example, a minimum current of 20 A (although lower currents may be applied if so desired) that may pass through the tumor during nsPEF application to have a desired effect of triggering tumor apoptosis. In order to prevent damage to tissues surrounding the tumor, the nsPEF therapy may be applied at a pulse frequency that will not heat the tissue above, e.g., 40° C. (the minimum temperature for hyperthermia effects). In one example, if 100 ns pulses were applied, the frequency of the applied pulses is desirably 7 pulses per second (Hz) or lower to prevent damage to surrounding tissues.

With the electrode assemblies described herein, treatment of tissue regions such as skin tumors may be effected by applying nsPEF while specifying various parameters. For instance, one or all of the following parameters may be adjusted to provide optimal treatment of tissue to effect tumor apoptosis: (1) pulse amplitude (kV/cm); (2) pulse duration (ns); (3) pulse application frequency (Hz); and/or (4) pulse number applied.

Because the value of these parameters may vary widely over a number of ranges, it has been determined that particular ranges may be applied for effecting optimal tissue treatment which may effect tumor apoptosis in as few as a single treatment. In varying pulse amplitude, an applied amplitude as low as, e.g., 20 kV/cm, may be sufficient for initiating an apoptotic response in the treated tissue. The pulse amplitude may, of course, be increased from 20 kV/cm, e.g., up to 40 kV/cm or greater. However, an applied amplitude of at least, e.g., 30 kV/cm or greater, may be applied for optimal response in the treated tissue. In varying pulse duration, durations in the range of, e.g., 50-900 ns, may be highly effective although shorter durations may be applied if the number of pulses is increased exponentially. In varying pulse application frequency, frequencies up to 7 Hz may be applied with 100 ns pulses without heating surrounding tissues to hyperthermic levels. Because tissue heating may be dependent on pulse width multiplied by the frequency of application, shorter pulses may be applied at proportionately higher frequencies with similar heat generation. In varying the number of pulses applied, the pulse number determines the total energy applied to the tissue region. Generally, applying a minimum pulse number of 600 pulses may result in complete remission of tumors. In one example, nsPEF therapy having a pulse duration of 100 ns may be applied over a range of, e.g., 1000-2000 pulses, to effectively treat the tissue region.

Given the range of parameters, a relationship between these parameters has been correlated to determine a minimum number of electrical pulses which may effectively treat a tissue region, e.g., a tumor, with a single treatment of nsPEF therapy to cause complete apoptosis in the tumor tissue. Generally, the number of electrical pulses increases exponentially as the pulse duration is shortened. The correlation for a given pulse duration or width and number of pulses, N, to effectuate complete tumor remission after a single treatment may be described in the following equation:

$$N=28,714e^{-0.026t}$$

where,

N=minimum number of pulses to cause tumor apoptosis with a single treatment t=pulse duration (in nanoseconds)

This non-linear dependence of pulse number on pulse width suggests that the effectiveness of the nsPEF therapy described herein is not simply due to energy delivery to the tumor as that is linearly proportional to N times t given a constant voltage and current.

DETAILED DESCRIPTION OF THE INVENTION

Figure 1:
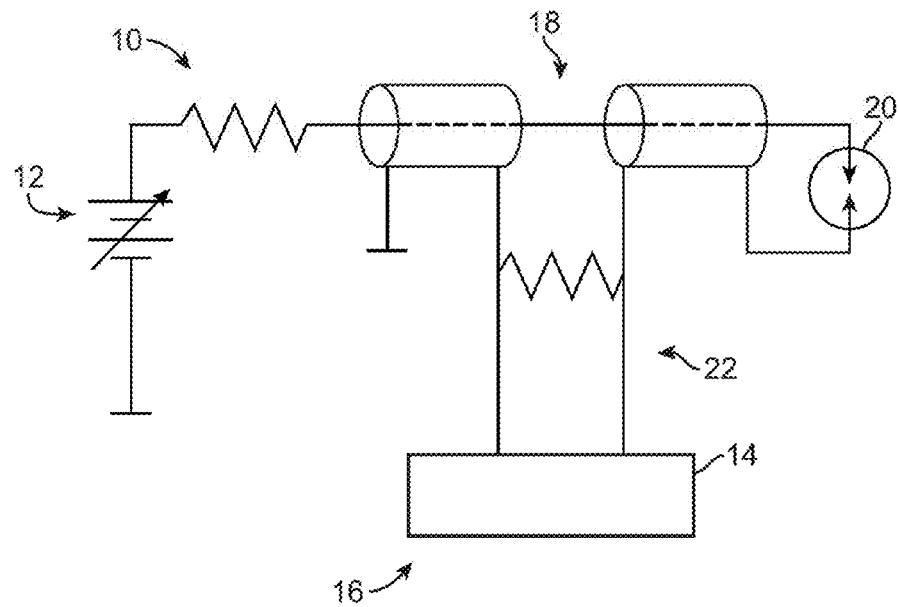
FIG. 1 illustrates a schematic diagram of an apparatus for generating a nanosecond pulsed electric field (nsPEF) for treating tumors.

As illustrated in the schematic of FIG. 1, an apparatus 10 (as described below) is illustrated schematically for intracellular electro-manipulation which includes a power supply 12 (a high voltage power supply, e.g., 40 kV or higher) and a delivery system 14 may be adapted to direct the electric pulse, particularly a nanosecond pulsed electric field (nsPEF), output to a load 16 such as target cells positioned in proximity to the delivery system 14. The pulse generator may include a pulse forming network 18 and a high voltage switch 20, such as a spark gap. The pulse forming network 18 may be a high voltage cable, a strip-line, or a pulse forming network constructed of individual capacitors and inductors in a transmission line arrangement with a matching network 22. The high voltage switch 20 can suitably be a gaseous, liquid or solid state switch, e.g., a spark gap. The energy in the pulse forming network 18 may be stored capacitively, which utilizes a closing switch 20 to release a pulse, or inductively, which requires an opening switch to release a pulse. Upon triggering of the switch 20, an electrical pulse is delivered through the delivery system 14 and launched into the load 16, e.g., the target cells in suspension or tissue form. The switch 20 can be triggered by a variety of common methods, e.g., optically or electrically.

The power supply 12 may utilize a high voltage DC power supply (e.g., Matsusada RB30-30P) to charge up, e.g., a coaxial cable (such as through a current limiting resistor), to a high voltage creating a capacitor on the coaxial cable between the inner conductor and its outer conductive shielding. When the inner conductor is rapidly brought to ground by a switch 20, a corresponding pulse of high voltage with, e.g., 15 ns rise and fall times, is generated across the load. The duration of this pulse may be determined by the length of cable used, and the amplitude may be determined by the voltage at which the coaxial cable was charged. Thus, in one variation, a coaxial cable having a length of, e.g., 20 meters, may be used to generate a pulse duration of, e.g., 100 ns.

By this method, it is possible to precisely control the number of pulses delivered as well as the frequency of those pulses simply by controlling the discharge switch for the coaxial cable's inner conductor. The generator 10 itself (including all components) may be sufficiently portable to fit into a rolling suitcase.

To control the system, a microcontroller such as a digital programmable logic device (e.g., Microchip PIC 16F887) may be incorporated into the assembly to control the pulse delivery. The user may input information to the microcontroller-based system via, e.g., a keypad, and a liquid crystal display (LCD) may be implemented to display information to the user. The circuit may be battery-powered.

The "load" 16, which includes the target cells in tissue or suspended in a medium, is placed between two or more electrodes. These electrodes may be solid material (in any of a number of suitable shapes, e.g., planar, cylindrical, spherical, etc), wires or meshes or combinations thereof. One (set of) electrode(s) is connected to the high voltage connection of the pulse generator, and a second (set of) electrode(s) is connected to the ground connection of the pulse generator in a suitable manner, e.g., via a second stripline or high voltage cable. The electrode material is a conductor, most commonly metal.

If such a pulse-forming network is charged up to, e.g., 18 kV, and then released, this charge can produce an almost rectangular ultra-short duration pulse which when applied to a load equal to twice the cable impedance can produce a maximum voltage of 18 kV. The corresponding electric field intensity between two electrodes separated by 1.0 mm is 180 kV/cm. The maximum electrical power, $V^2/R$, which can be achieved with these conditions is 3.24 MW (assuming R=100Ω), while the energy (power×pulse duration) transferred into the load is only 0.32 Joule if the pulse duration is 100 ns. For a 100 μL volume of cell suspension, this energy transfer results in a calculated maximum temperature increase of only about 1 K for a single pulse.

As mentioned above, in applying a nanosecond pulsed electric fields (nsPEF) an electrode assembly may be utilized. An example of some electrode assemblies which may be utilized are shown and described in further detail in U.S. Prov. Pat. App. 60/916,898 filed May 9, 2007 (and in corresponding WO 2008/141221 A1), each of which are incorporated herein by reference in its entirety.

In one variation of an electrode, a medical instrument for delivering electrotherapy illustratively comprises an outer support member having an open distal end and a base wall portion within the support member arranged to form a cup-like open volume in the distal end of the support member. At least one aperture is formed in the cup-like volume for applying a suction mechanism to the cup-like region. At least a first and a second electrode have at least a portion extending into the cup-like region. A system for delivering electrotherapy comprises a medical instrument having a suction mechanism for providing a source of suction within the cup-like volume to hold a tissue portion to be treated, and a power supply coupled to the first and second electrodes for applying electrical signals to provide electrotherapy to the tissue. When the tissue or tumor to be treated is adhered to the instrument by the suction mechanism, the tumor may be positioned in apposition to the electrode assembly for effectively delivering the pulses. A variety of pulse generators can be used. However, the pulse generator is desirably capable of delivering high voltage pulses (e.g., in the 1-900 ns range) which are imposed across a pair of spaced apart electrodes, to generate electrical fields on the order of, e.g., 20 to 100 kV/cm.

The electrode assembly may be designed to draw tissue into the recessed cup-like volume in order to immobilize the tissue and position the electrodes firmly against or within the tissue. This allows for desirable targeted treatment of the tissue. For positioning electrodes against the tissue, flat (planar) electrodes can be positioned along the inner walls of the cup-like volume. For positioning electrodes within the tissue, needle-like electrodes protruding essentially perpendicular from the backside portion of the cup-like volume can be provided for penetrating a controllable constant distance into the tissue as it is drawn into the recessed cup-like volume.

Figures 2A, 2B, 2C, 2D:
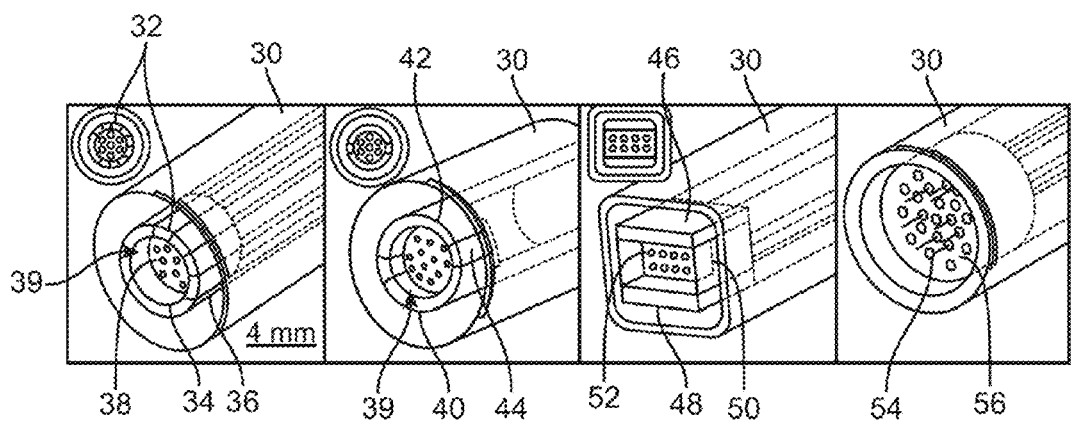
FIGS. 2A to 2F illustrate perspective views of variations of electrode assemblies which may be used to apply the nsPEF upon tissue adhered via a retaining mechanism, such as a suction mechanism.

FIGS. 2A to 2D show variations of electrode assemblies for delivering electrotherapy using suction electrodes. The electrode assemblies may utilize stainless steel electrodes which are electropolished to eliminate any sharp edges that can lead to corona formation at high voltages and are then embedded in a dielectric material, such as a plastic. Very small holes 38 may be formed or drilled into the base of the recessed cavity 39 and during use a suction may be applied through the holes to draw the tissue to be treated into the recessed cavity 39, e.g., cup-like volume having an inner diameter of about 4 mm and a depth of about 2 mm, for electric field application. The dimensions of recessed cavity 39 are intended to be illustrative and not limiting. Accordingly, recessed cavity 39 may be varied in its size to match a size of any particular tumor to be treated such that the treated tumor may be received within the cavity in close proximity or in direct contact against the electrodes. FIG. 2A shows an example of an electrode assembly comprising a support member 30 having a cylindrical cross section having, e.g., six (6) spaced apart planar electrodes 32, positioned circumferentially about the recessed cavity 39. The electrodes 32 are electrically isolated from one another by a dielectric material 34, such as plastic upon which the electrodes can be, e.g., partially embedded. In the arrangements shown the electrodes 32 have one exposed side (without plastic) along the wall of the cavity 39 to allow direct contact to the skin. The opposite sides of the electrode 32 may be coated with plastic. In operation, electrodes in apposition from one another form bias pairs. A plurality of apertures 38 in the back plate 36 are shown for applying a suction force to immobilize a region of skin or epithelium therein.

FIG. 2B shows another variation of the electrode assembly comprising support member 30 having a cylindrical cross section and having a pair of "U"-shaped planar electrodes 40 and 42 disposed on the periphery of the recessed cavity 39.

The electrodes 40, 42 may be electrically isolated from one another by a dielectric material, such as plastic 44 upon which the electrodes can be embedded. FIG. 2C shows another variation comprising a support member 30 having a rectangular cross section and having a pair of spaced apart parallel plate electrodes 46 and 48. The back plate 50 having a plurality of apertures 52 therein may be formed from a dielectric material. FIG. 2D shows another variation comprising a support member 30 having a plurality of needle electrodes 54 which are mounted at the base of the back plate 56 to control the penetration depth of the tissue as it is sucked into the cup-shaped volume. The distance between the center needle and each of the four outer needles may vary but is shown in this example as about 2 mm.

Figure 2E:
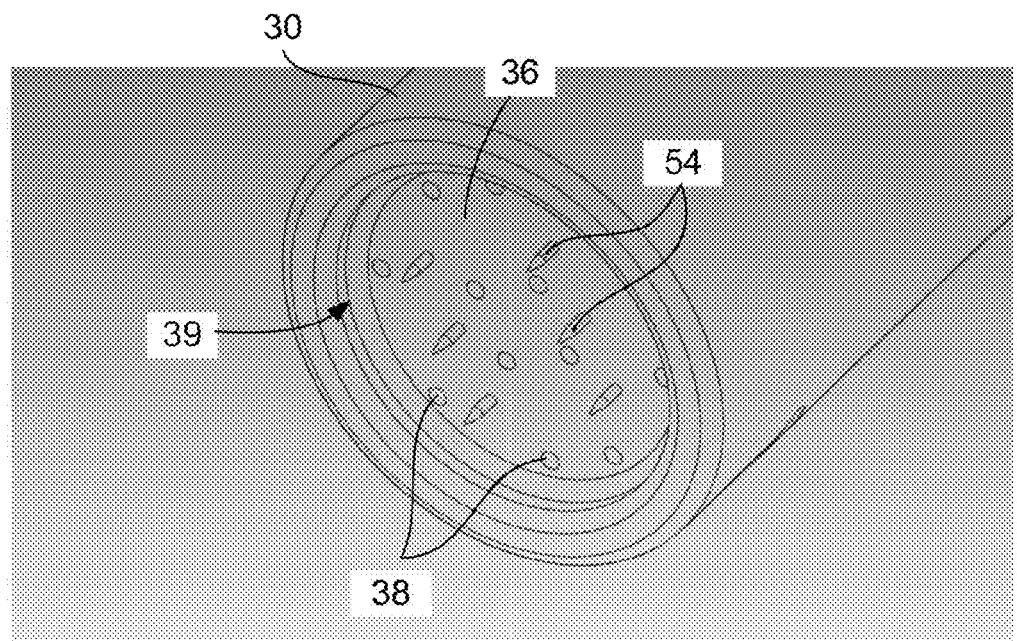
Figure 2F:
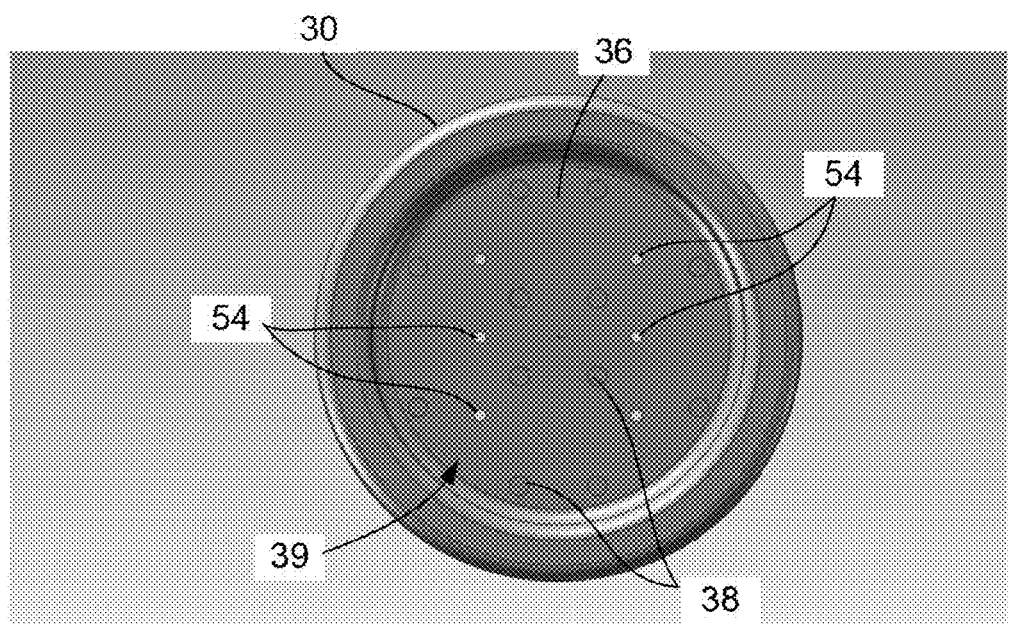

FIGS. 2E and 2F show perspective and end views, respectively, of yet another variation of an electrode assembly. In this example, support member 30 may also define the recessed cavity 39 and the plurality of apertures 38 defined over the back plate 36. A plurality of needle electrodes 54, e.g., six (6) needle electrodes, may project into the cavity 39 from the back plate 36 with the needle electrodes 54 arranged in a parallel array. In this variation, a linear arrangement of three (3) needle electrodes 54 may be aligned in parallel with an adjacent linear arrangement of three (3) needle electrodes 54, as shown, with the apertures 38 positioned about the electrode array.

Since each electrode is electrically isolated from one another, electrodes can be connected to separate electrically conductive (e.g. copper) wires, such as wires that end on a connector projecting out of the side of the plastic cylinder. This allows each electrode to be connected to a different pulse generator and biased differently for maximum versatility, if so desired.

As previously mentioned, the back plate of each recessed cavity may have multiple apertures, such as on the order of 100 μm in diameter. An air pump, e.g., an oscillating diaphragm air pump or other suction source, is then coupled to the support member on the side of the base wall support opposite the recessed cavity and is used to generate a mild suction that pulls the tissue to be treated into the cup-like volume.

The electrodes may comprise an electrical conductor that is resistant to corrosion such as, for example, stainless steel. The electrodes portioned at the distal end are preferably electropolished or otherwise planarized. Electropolishing removes corners and sharp edges to minimize undesirable corona discharge when large voltages associated with generating nsPEF are applied to the electrodes.

In utilizing the generated nsPEF through any one of the electrode assemblies to treat tumors, such as melanoma tumors, the parameters in above-described U.S. Pat. No. 6,326,177 are generally insufficient in effectively treating such tumors. The disclosed number of pulses, i.e., 20 pulses, at 100 ns is insufficient; rather, 1500 pulses at 100 ns instead would be optimal for treating such tumors.

Figures 3A, 4A, 5A:
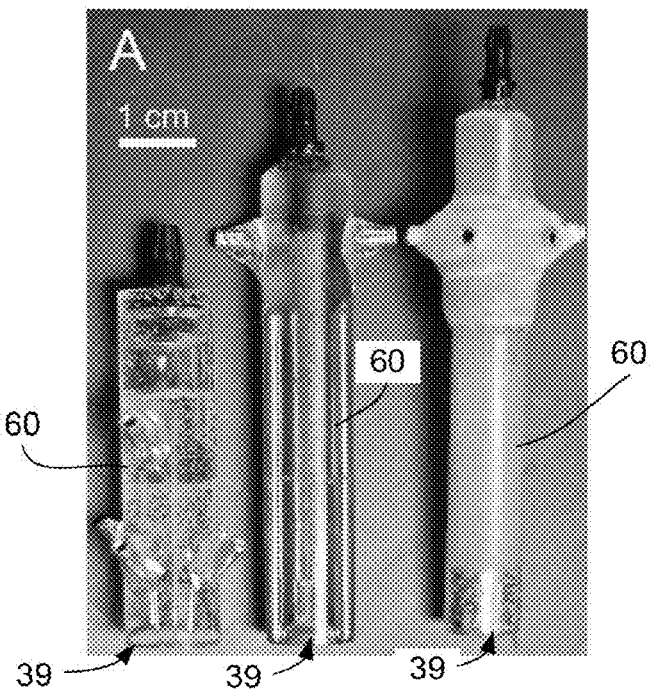
FIGS. 3A and 3B show side and perspective views, respectively, of an exemplary suction electrode assembly having a plurality of needle electrodes projecting into a recessed cavity.
FIGS. 4A and 4B show side and perspective views, respectively, of another variation of the suction electrode assembly having two apposed electrodes positioned on either side of the recessed cavity.
FIGS. 5A and 5B show side and perspective views, respectively, of yet another variation of the suction electrode assembly having at least six circumferentially positioned electrodes around the recessed cavity.
Figures 3B, 4B, 5B:
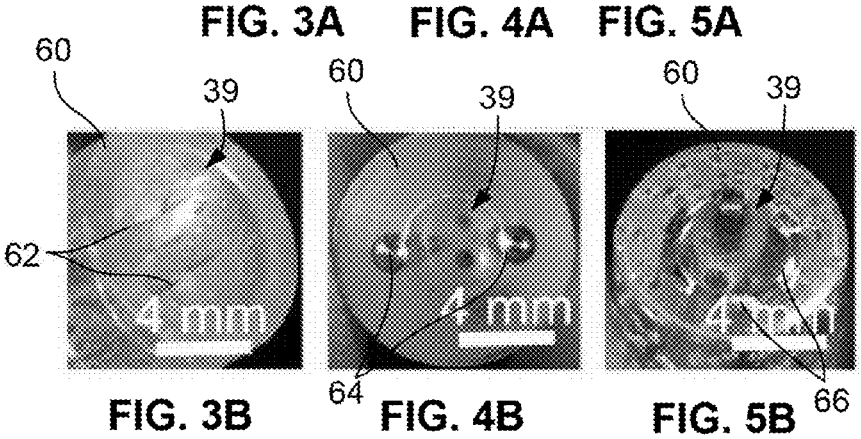

Turning now to FIGS. 3A, 4A, and 5A, side views of exemplary suction electrodes developed for use and experimentation are shown. FIGS. 3B, 4B, and 5B show corresponding perspective views of the electrode treatment distal end effectors. Each support member 60 may be seen having a recessed cavity 39 for contacting and receiving the tissue to be treated. FIG. 3B illustrates the recessed cavity 39 of support member 60 having a plurality of needle electrodes 62, as previously described. FIG. 4B illustrates the recessed cavity 39 having at least two electrodes 64 positioned in apposition on either end of the cavity 39 for treating the tissue region positioned therebetween and FIG. 5B illustrates a variation having at least six electrodes 66 electrically isolated from one another and positioned about a circumference of recessed cavity 39, as previously described.

Figure 6A:
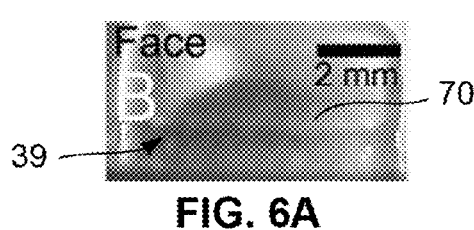
FIGS. 6A to 6D illustrate side views of various tissue regions drawn into the recessed cavity for tissue treatment via nsPEF application.
Figure 6B:
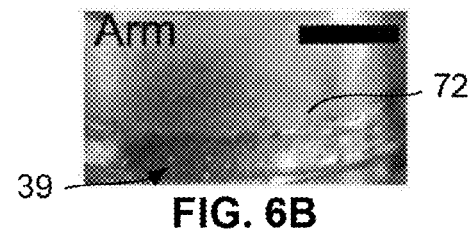
Figure 6C:
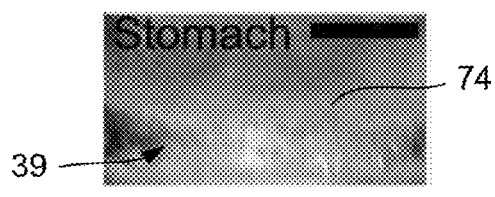
Figure 6D:
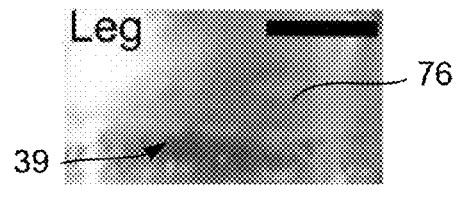

In use, FIGS. 6A to 6D show side views of the support member 60 suctioning or drawing in tissue to be treated from various regions of the body to illustrate how the tissue may be drawn into the recessed cavity 39 into contact or proximity to the electrodes. Drawing in the tissue may further facilitate tissue treatment by clearly defining the treatment area to be treated for the operator. As shown in FIG. 6A, a region of tissue 70 from a subject's face may be readily drawn into recessed cavity 39. FIG. 6B illustrates a region of tissue 72 from a subject's arm, FIG. 6C illustrates a region of tissue 74 from a subject's stomach, and FIG. 6D likewise illustrates a region of tissue 76 to be treated from the subject's leg.

Figure 7:
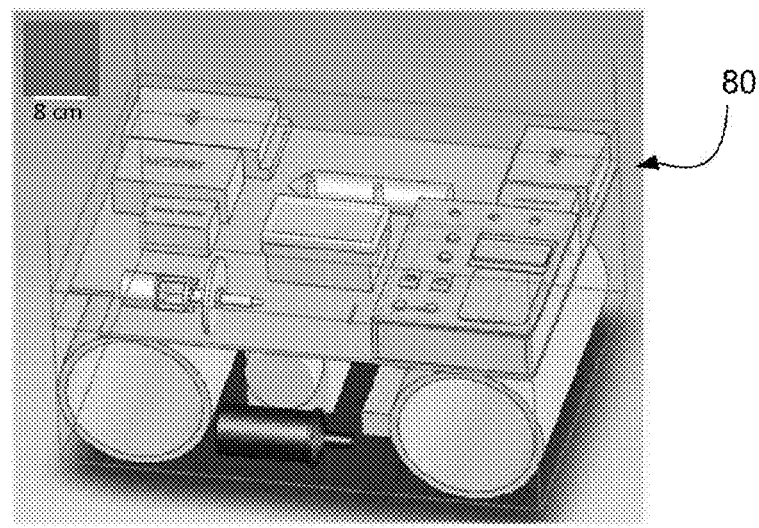
FIG. 7 shows a perspective view of an example of a portable nsPEF treatment assembly readied for transportation or shipping.
Figure 8:
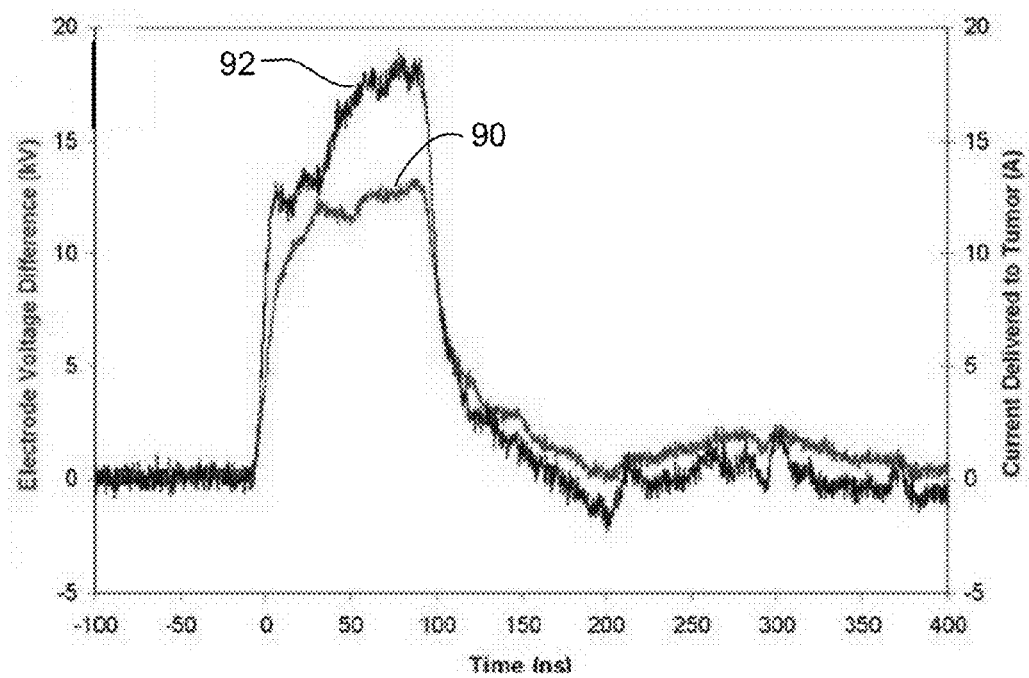
FIG. 8 shows a graph of the applied, pulse voltage with a rise time of, e.g., 15 ns and the current waveform delivered to the treated tissue.

Because the components of the assembly are portable, the assembly may be stored or housed in a housing 80 for ready shipping or transportation, as shown in FIG. 7. An example is shown in the graph of FIG. 8 of the applied pulse voltage 90 having a rise time of, e.g., 15 ns in this particular example, and the resulting current waveform 92 delivered to the tissue region, e.g., tumor, when utilizing an electrode treatment assembly having a six-electrode configuration, as previously described.

When nsPEF is applied to a tissue region such as a tumor, if a large resistance between the electrode and the tumor restricts current flow (such as the presence of the stratum corneum in skin), the field may not pass into the tumor effectively. Thus it may be desirable to apply, in one example, a minimum current of 20 A (although lower currents may be applied if so desired) that may pass through the tumor during nsPEF application to have a desired effect of triggering tumor apoptosis. In order to prevent damage to tissues surrounding the tumor, the nsPEF therapy may be applied at a pulse frequency that will not heat the tissue above, e.g., 40° C. (the minimum temperature for hyperthermia effects). In one example, if 100 ns pulses were applied, the frequency of the applied pulses is desirably 7 pulses per second (Hz) or lower to prevent damage to surrounding tissues.

With the electrode assemblies described herein, treatment of tissue regions such as skin tumors may be effected by applying nsPEF while specifying various parameters. For instance, one or all of the following parameters may be adjusted to provide optimal treatment of tissue to effect tumor apoptosis: (1) pulse amplitude (kV/cm); (2) pulse duration (ns); (3) pulse application frequency (Hz); and/or (4) pulse number applied.

Because the value of these parameters may vary widely over a number of ranges, it has been determined that particular ranges may be applied for effecting optimal tissue treatment which may effect tumor apoptosis in as few as a single treatment. In varying pulse amplitude, an applied amplitude as low as, e.g., 20 kV/cm, may be sufficient for initiating an apoptosis response in the treated tissue. The pulse amplitude may, of course, be increased from 20 kV/cm, e.g., up to 40 kV/cm or greater. However, an applied amplitude of at least, e.g., 30 kV/cm or greater, may be applied for optimal response in the treated tissue. In varying pulse duration, durations in the range of, e.g., 50-900 ns, may be highly effective although shorter durations may be applied if the number of pulses is increased exponentially. In varying pulse application frequency, frequencies up to 7 Hz may be applied with 100 ns pulses without heating surrounding tissues to hyperthermic levels. Because tissue heating may be dependent on pulse width multiplied by the frequency of application, shorter pulses may be applied at proportionately higher frequencies with similar heat generation. In varying the number of pulses applied, the pulse number determines the total energy applied to the tissue region. Generally, applying a minimum pulse number of 600 pulses may result in complete remission of tumors. In one example, nsPEF therapy having a pulse duration of 100 ns may be applied over a range of, e.g., 1000-2000 pulses, to effectively treat the tissue region.

Given the range of parameters, a relationship between these parameters has been correlated to determine a minimum number of electrical pulses which may effectively treat a tissue region, e.g., a tumor, with a single treatment of nsPEF therapy to cause complete apoptosis in the tumor tissue. Generally, the number of electrical pulses increases exponentially as the pulse duration is shortened. Data obtained and as shown in the following Table 1 shows the minimum number of pulses which may be applied for a given pulse width to completely eliminate, e.g., a melanoma, with a single nsPEF treatment utilizing the devices described herein.

TABLE 1

Pulse duration or width (ns) vs. number of pulses to eliminate a tumor.

| Pulse duration (ns) | Pulses required to eliminate tumor |
|---|---|
| 25 | 15000 |
| 50 | 8000 |
| 100 | 2000 |
| 300 | 600 |

Figure 9:
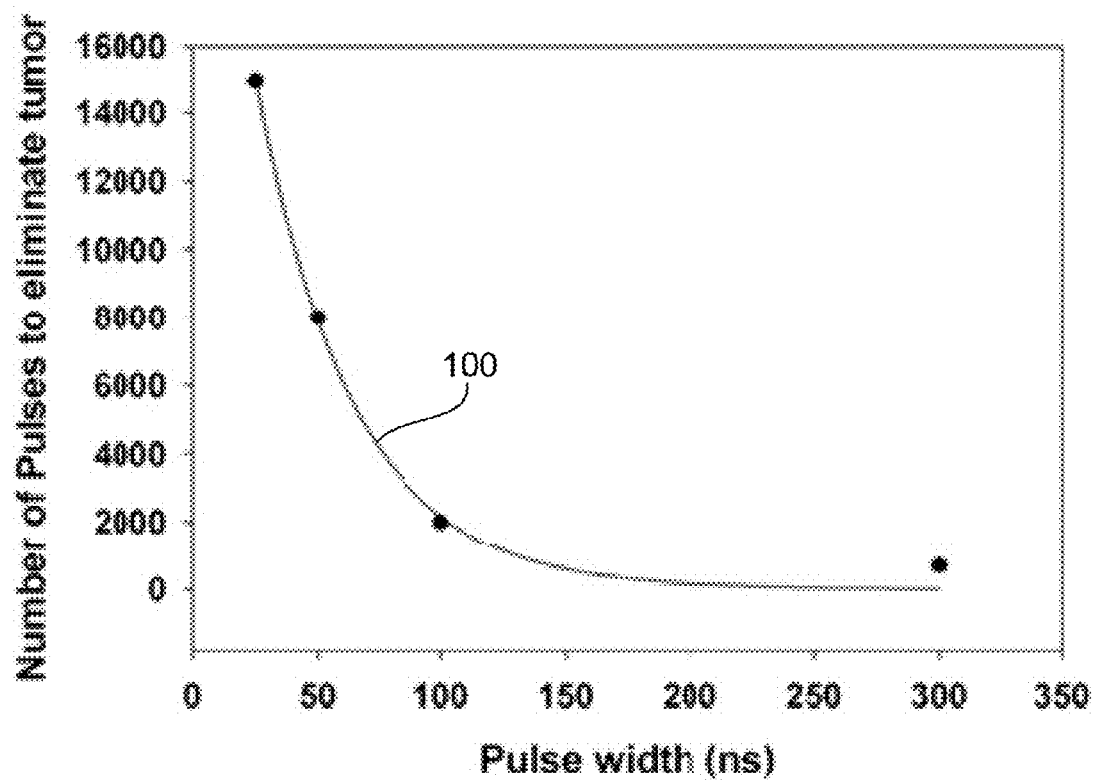
FIG. 9 shows a graph illustrating the correlation for a given pulse duration or width and number of applied pulses to eliminate tumors in, e.g., a single treatment.

The values of Table 1 are plotted in the chart of FIG. 9 and provides a correlation illustrated by curve 100 where for a given pulse duration or width, any number of pulses, N, at or above the curve 100 may result in complete tumor remission after a single treatment as described herein. The curve 100 may be described in the following equation (1):

$$N = 28{,}714 e^{-0.026 t} \quad (1)$$

where,

N=minimum number of pulses to cause tumor apoptosis with a single treatment t=pulse duration (in nanoseconds)

This non-linear dependence of pulse number on pulse width suggests that the effectiveness of the nsPEF therapy described herein is not simply due to energy delivery to the tumor as that is linearly proportional to N times t given a constant voltage and current.

EXAMPLE 1

Figure 10:
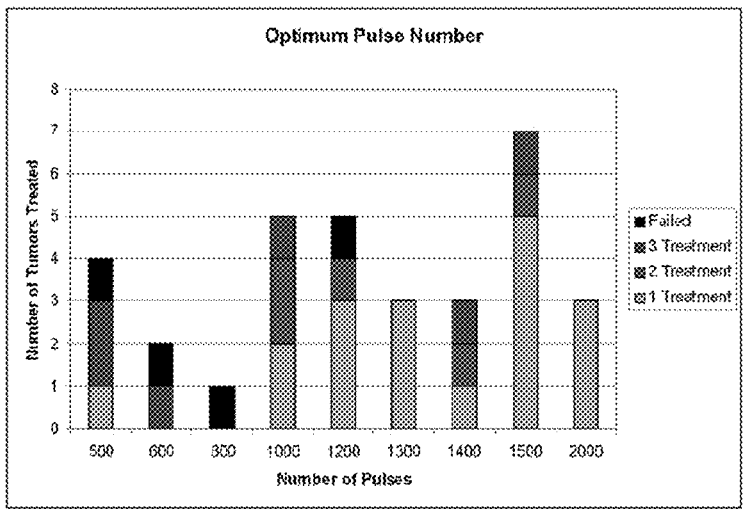
FIG. 10 illustrates a chart of the Optimum Pulse Number where a majority of tumors were successfully treated with no signs of resurgence after a single treatment when pulsed with at least 1500 to 2000 pulses.
Figure 11:
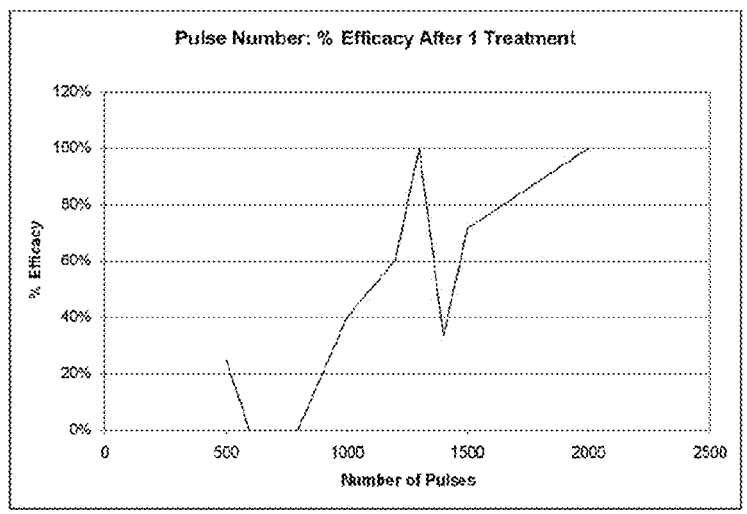
FIG. 11 illustrates a chart of the Percent Efficacy after one treatment where the efficacy is shown to increase from 1500 pulses and higher.

In optimizing the device, multiple experiments have shown that tumors, such as melanoma tumors, may be eliminated utilizing nsPEF when exposed to 100 ns long pulses having a 15 ns rise time where the minimum number of pulses range from, e.g., 1500 to 2000 pulses, as illustrated in the chart of FIG. 10 which shows the Optimum Pulse Number where a majority of tumors were successfully treated after a single treatment when pulsed with at least 1500 to 2000 pulses. Accordingly, as shown in the graph of FIG. 11, the Percent Efficacy after one treatment is shown to increase from 1500 pulses and higher.

Figure 12:
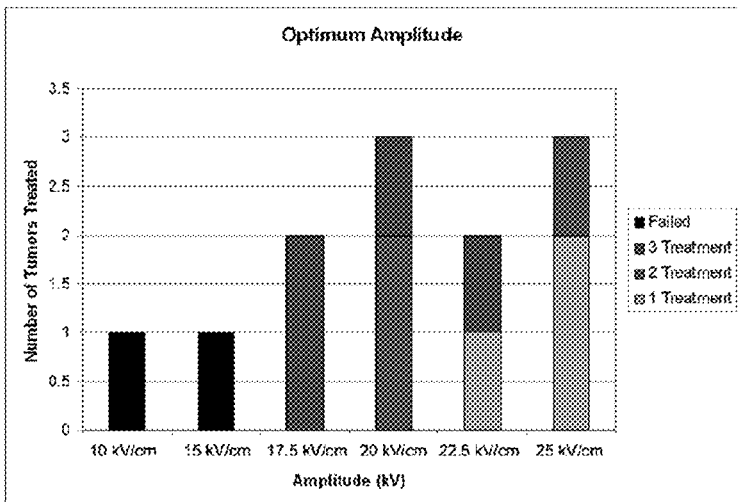
FIG. 12 illustrates a chart of the Optimum Amplitude of the pulses where the number of tumors successfully treated after a single treatment increases at higher amplitudes.

As also indicated in the chart of FIG. 12 which illustrates Optimum Amplitude of the pulses, the number of tumors successfully treated after a single treatment begins to rise at higher amplitudes, e.g., from 25 kV/cm. Thus, the minimum pulse amplitude observed is 30 kV/cm in this example while the optimum pulse amplitude is 40 kV/cm or greater in this example for effectively treating tumors such as melanoma tumors.

Aside from pulse amplitude, another parameter is pulse frequency. It has been determined that the optimum pulse frequency is 7 Hz as higher frequencies may result in excessive heat applied to the tissue, as previously described. Thus, if a maximum frequency of 7 Hz were utilized to deliver at least 2000 pulses, the treatment time to optimally treat a tumor would be at least 4 to 5 minutes at about, e.g., 4.76 minutes. In utilizing the parameters described above for the nsPEF, a treated tumor may be effectively eliminated within a week or two following a single application of the nsPEF. Additional treatments of the tumor or tumors may be effected if necessary or desired.

EXAMPLE 2

In this particular example, Murine B16-F10 melanoma cells transfected with enhanced green fluorescent protein (eGFP) were obtained and stored in liquid nitrogen until use. These cells were cultured and injected into 4-6 week old female Nu/Nu mice (immunodeficient, hairless, albino) using standard procedures at four injection sites each. Tumors were detected visually by the bulges they produced and by GFP detection under fluorescent microscopy.

Figures 13, 14:
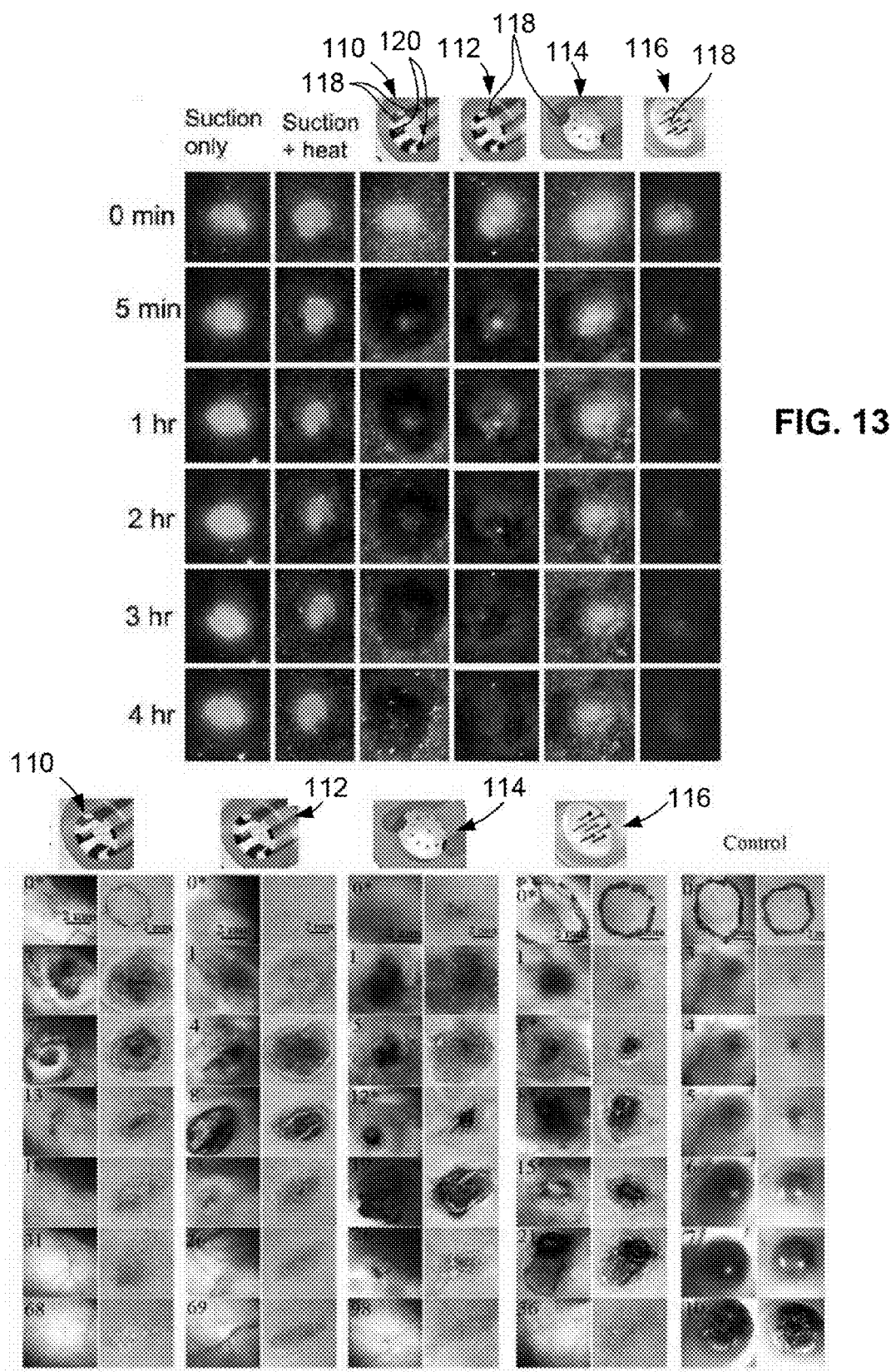
FIG. 13 shows a chart recording tumor detection via GFP detection under fluorescent microscopy for tissue treated via nsPEF therapy with various electrode assemblies.
FIG. 14 shows a chart recording trans-illumination and reflected light images adjacent to one another of the treated tissues (melanomas) corresponding to the various electrode assemblies.

Various suction electrode assemblies, shown in FIG. 13, were used where electrode assemblies 110, 112, and 114 each had a recessed cavity with an inner diameter of about 4 mm and a depth of about 2 mm while the electrode assembly 116 utilized an array of needles positioned within the recessed cavity where a distance between the center needle and each of the outer needles was about 2 mm. In each of the assemblies, one or more electrodes 118 were used to discharge the energy into the treated tissue while the remaining electrodes functioned as return electrodes.

A suction was drawn (e.g., 500 mm Hg) within the recessed cavity to pull the tumor therein and nsPEF therapy was applied with 100 ns pulse widths while either the pulse number, amplitude, or frequency was varied. A typical treatment applied 2700 pulses with a pulse width of 100 ns at 30 kV/cm and a frequency of 5-7 Hz. The suction electrode assembly was rotated 45° every 500 pulses to ensure uniform field distribution across the tumor.

GFP fluorescence changes following nsPEF application using the electrode pictured at the top of each column were noted at 0 min, 5 min, 1 hr, 2 hr, 3 hr, and 4 hr. GFP fluorescence changes, if any, were also noted for tumors which had only suction applied as well as suction plus heat applied (37° C. for 10 min) but without nsPEF treatment. FIG. 13 shows the resulting tumor activity for each of the electrode assemblies 110, 112, 114, and 116. Tumors that showed signs of regrowth, generally indicated by renewed GFP production, were retreated using the same parameters as the first treatment. Tumors were considered eliminated when no regrowth was detected within two weeks after the last treatment.

FIG. 14 also shows trans-illumination and reflected light images adjacent to one another of the treated tissues (melanomas) corresponding to the various electrode assemblies 110, 112, 114, and 116. The images were recorded on the days indicated in the upper left corner of each pair of figures, e.g., 0, 3, 7, etc., where nsPEF treatment (if applied) occurred on day 0.

Figure 15:
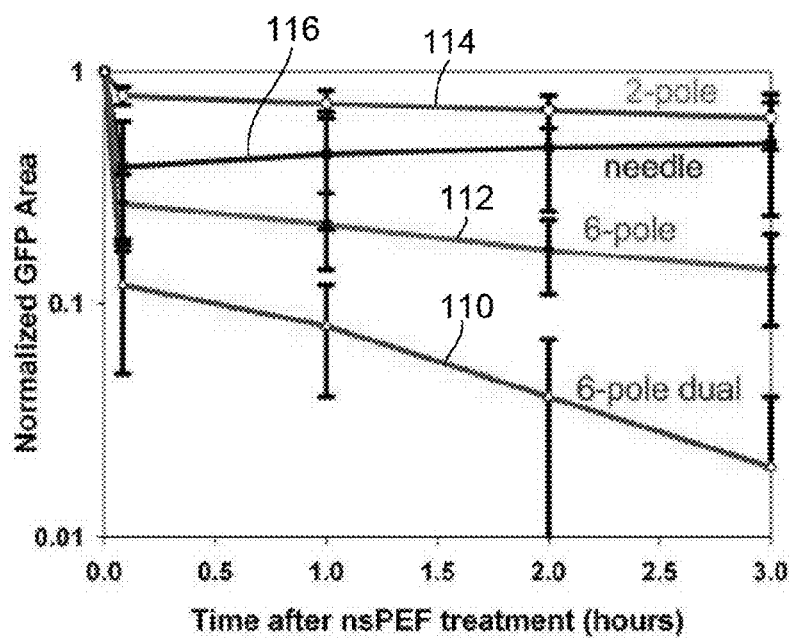
FIG. 15 shows a chart with the measured change in GFP signal area normalized on a logarithmic scale over a period of time following nsPEF treatment with various electrode assemblies.
Figure 16:
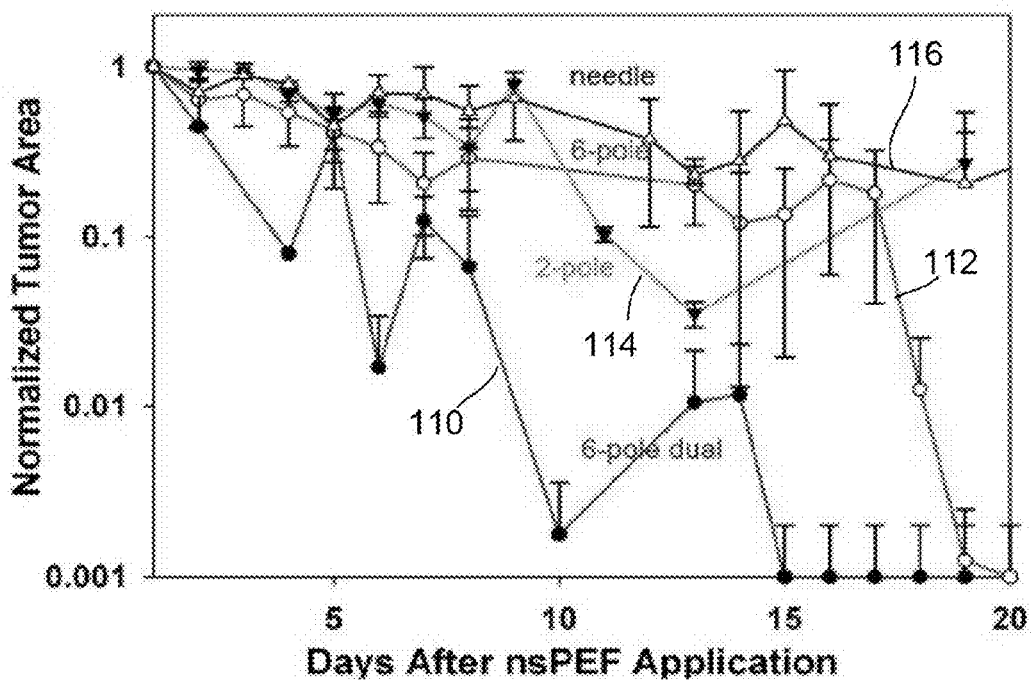
FIG. 16 shows a chart with the measured change in tumor area normalized on a logarithmic scale over a period of days following nsPEF treatment with various electrode assemblies.

FIG. 15 shows the measured change in GFP signal area normalized on a logarithmic scale over a period of time in hours following nsPEF treatment with the indicated suction electrode type, i.e., the 6-pole dual plot correlates to electrode assembly 110, the 6-pole plot correlates to electrode assembly 112, the 2-pole plot correlates to electrode assembly 114, and the needle plot correlates to electrode assembly 116. The indicated error bars represent the standard error of the mean (SEM) with N=10-12. FIG. 16 shows the measured change in tumor area normalized on a logarithmic scale over a period of days following nsPEF treatment with the indicated suction electrode type assembly. As above, the indicated error bars represent a standard error (SEM) of N=10-12.

Figure 17:
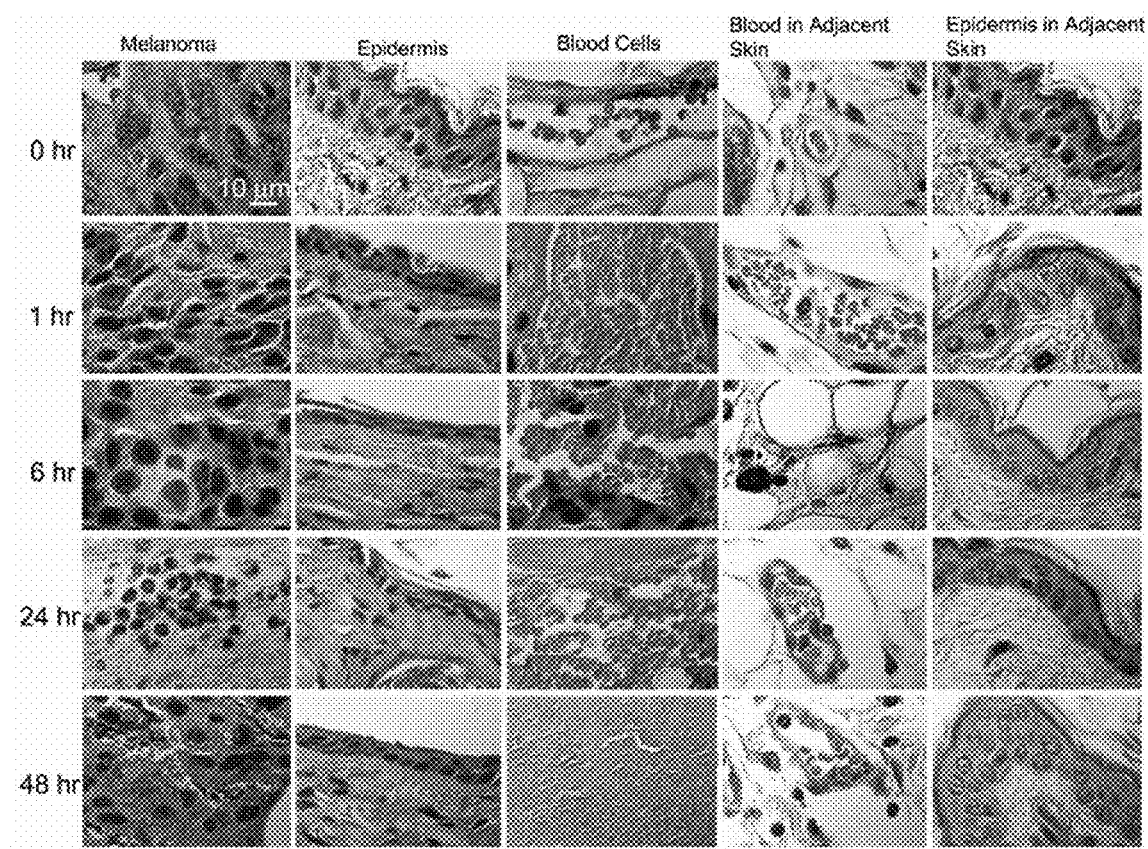
FIG. 17 shows histological sections of the treated tumors and skin immediately adjacent to suction electrode location taken at different times after nsPEF treatment.

As shown in FIG. 17, histological sections of the treated tumors and skin immediately adjacent to suction electrode location were taken at different times after treatment with 2000 pulses at 30 kV/cm and a frequency of 7 Hz. Images in the three left columns were taken from skin (melanoma, epidermis, and blood cells) with tumors before (i.e., 0 hr) and several times after nsPEF treatment (i.e., at 1 hr, 6 hrs, 24 hrs, and 48 hrs). Images in the two right columns were taken from skin (blood in adjacent skin and epidermis in adjacent skin) immediately adjacent to the nsPEF-treated region and no morphological changes could be detected there indicating that the nsPEF treatment effects on skin and melanomas are highly localized to the region between the electrodes.

Figure 18:
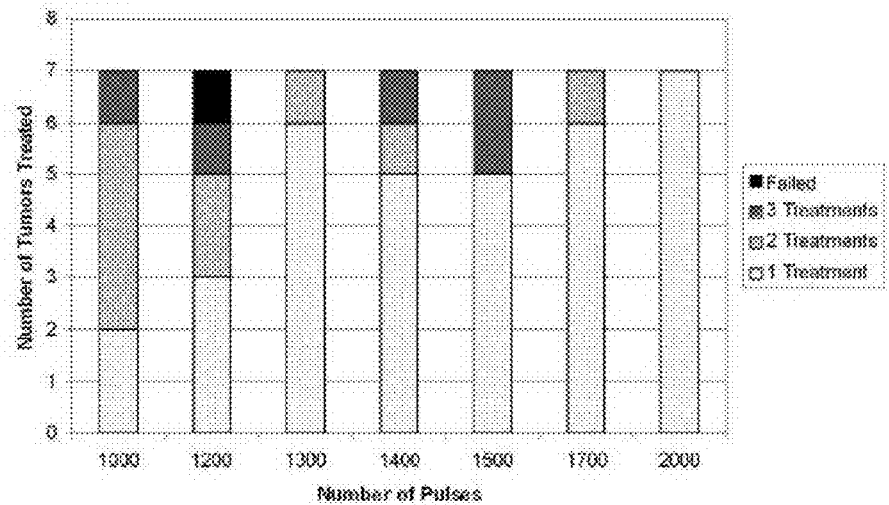
FIG. 18 shows a chart indicative of the number of tumors treated along with the number eliminated (e.g., by 1, 2, or 3 treatments) relative to the number of pulses applied during nsPEF treatment.
Figure 19:
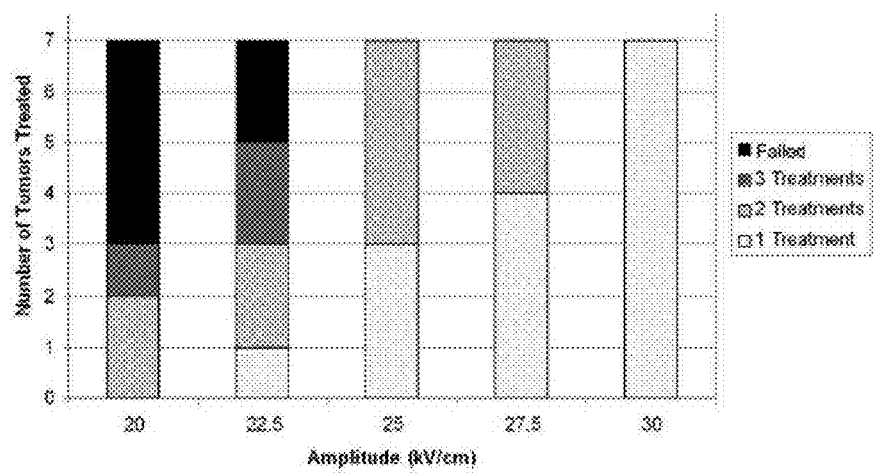
FIG. 19 shows a chart indicative of the number of tumors treated along with the number eliminated (e.g., by 1, 2, or 3 treatments) relative to the pulse amplitude applied during nsPEF treatment.
Figure 20:
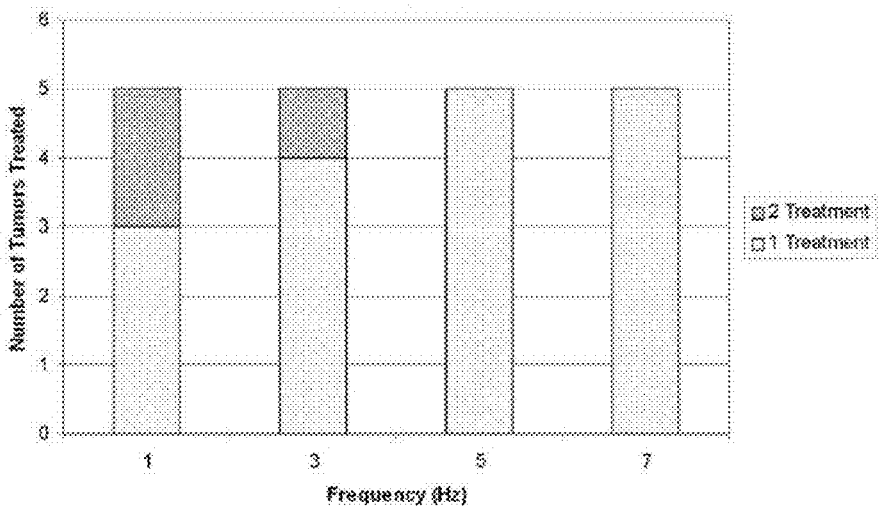
FIG. 20 shows a chart indicative of the number of tumors treated along with the number eliminated (e.g., by 1, 2, or 3 treatments) relative to the pulse frequency applied during nsPEF treatment.

Thus, in varying the range of pulse numbers from 500-2700 while using the same amplitude (e.g., 30 kV/cm), duration (e.g., 100 ns), and frequency (e.g., 5 Hz), a minimum of 2000 pulses has shown desirable complete elimination of tumors, although fewer pulses may be applied if desired, as indicated in the chart of FIG. 18. In varying the range of pulse amplitude while using the same pulse duration (e.g., 100 ns), pulse number (e.g., 2000 pulses), and frequency (e.g., 7 Hz), a minimum amplitude of 30 kV/cm has shown desirable elimination of tumors, although the amplitude may be lowered or increased if so desired, as indicated in the chart of FIG. 19. In varying the range of pulse frequency, it is generally desirable to use the highest pulse application frequency possible without damaging the surrounding tissue given the temperature rise in the tissue, as indicated in the chart of FIG. 20. Applying nsPEF at 1 Hz at 30 kV/cm and 20 A to tissue may increase the tumor temperature by 2° C. whereas 5 Hz increased the tumor temperature by 6-7° C. Applying a frequency of 7 Hz may limit the temperature rise of the treated tissue to 37° C. which is below the hyperthermia threshold of 41° C. For an amplitude of 30 kV/cm, applying pulses at 5 Hz or higher was more effective than using lower frequencies.

EXAMPLE 3

Figure 21:
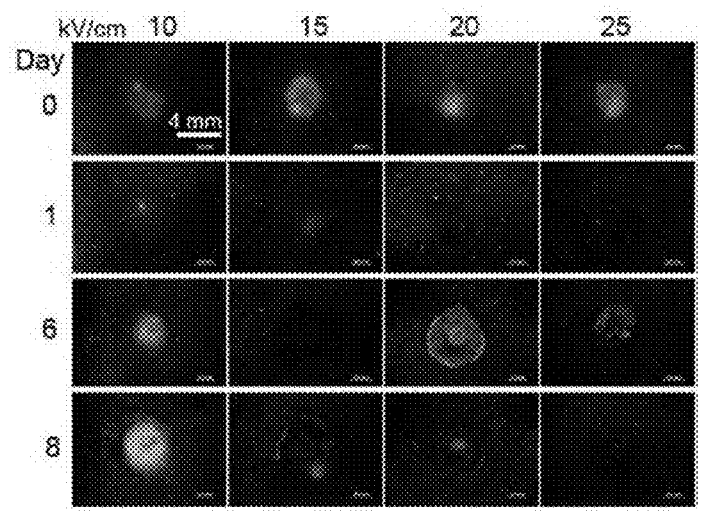
FIG. 21 shows a chart recording tumor detection via GFP detection under fluorescent microscopy for tissue treated via nsPEF at various amplitudes.
Figure 22:
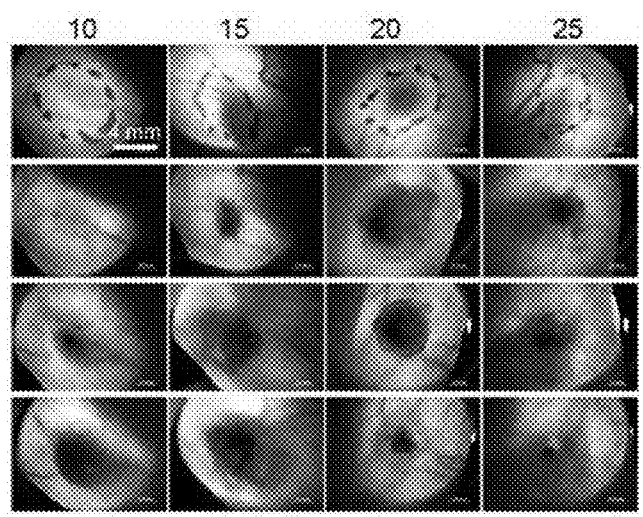
FIG. 22 shows a chart recording trans-illumination images of treated tissue at various amplitudes.
Figure 23:
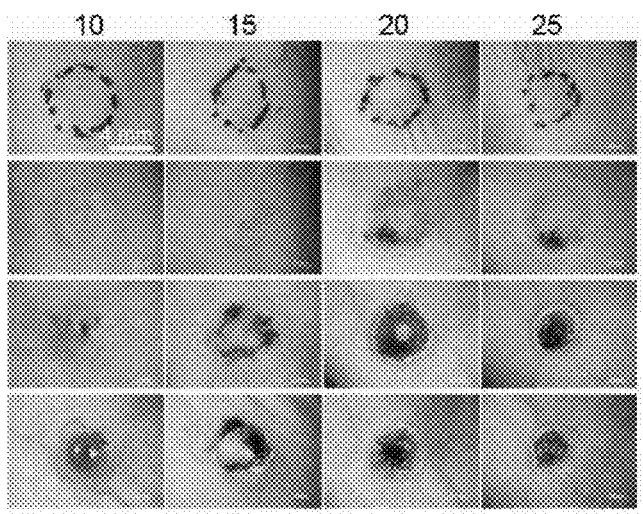
FIG. 23 shows a chart recording reflected light images of treated tissue at various amplitudes.
Figure 24:
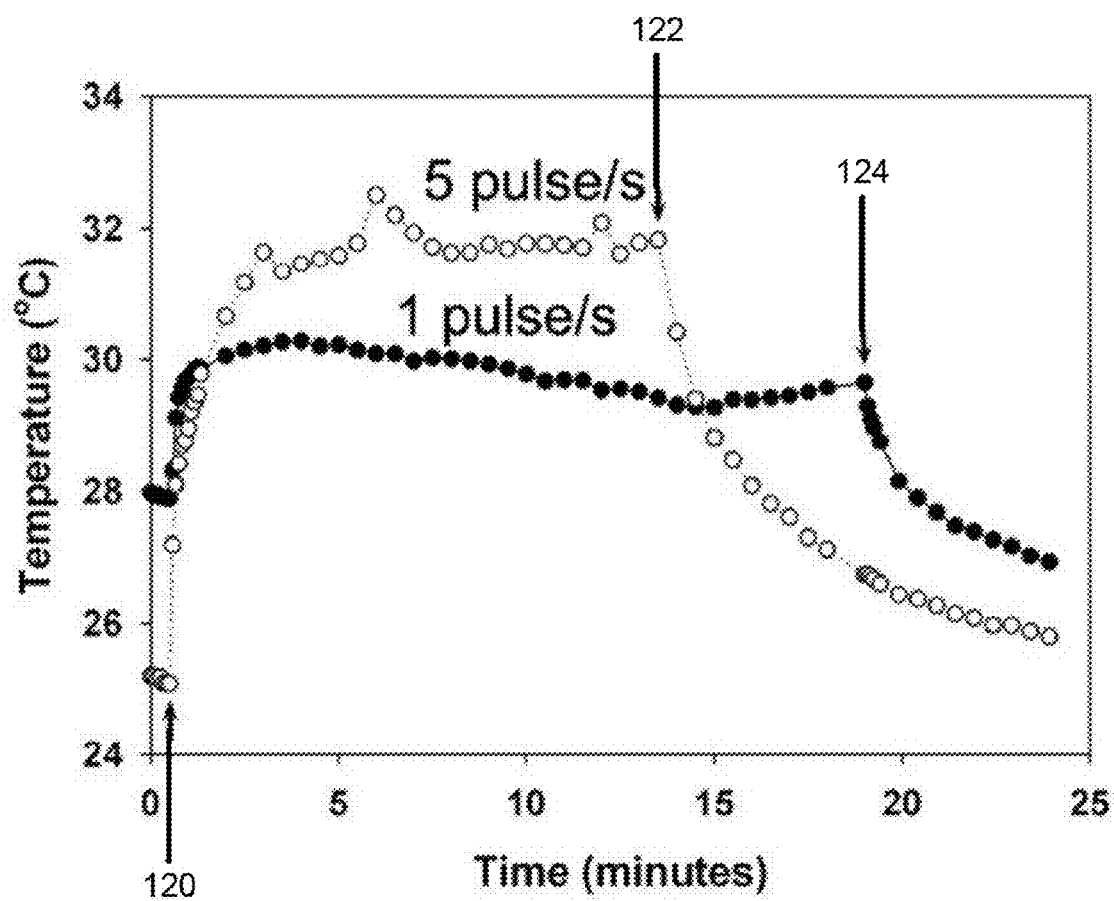
FIG. 24 shows a chart recording the temperature increase within a tumor over a period of several minutes during nsPEF treatment.

Typical melanoma responses to nsPEF therapy in the 10-25 kV/cm range were recorded where four melanomas on one mouse were treated with either 10, 15, 20 or 25 kV/cm nsPEF (2000 pulses, 100 ns, 7 Hz). The GFP fluorescence at each respective pulse amplitude over a period of 0, 1, 6, and 8 days were recorded, as shown in FIG. 21, as were the trans-illumination, as shown in FIG. 22, and reflected light images, as shown in FIG. 23. The temperature increase inside a tumor over a period of several minutes during nsPEF application were also recorded, as shown in FIG. 24.

A pulse amplitude of 30 kV/cm with 100 ns long pulses were applied beginning at the indicated frequency 120 with frequency of 1 Hz and 5 Hz. Pulsing was stopped at the indicated frequency 122 for 5 Hz and at 124 for 1 Hz. The 1 Hz pulse application increased tumor temperature by 2° C. while the 5 Hz pulse application increased the temperature by 7° C.

Figure 25:
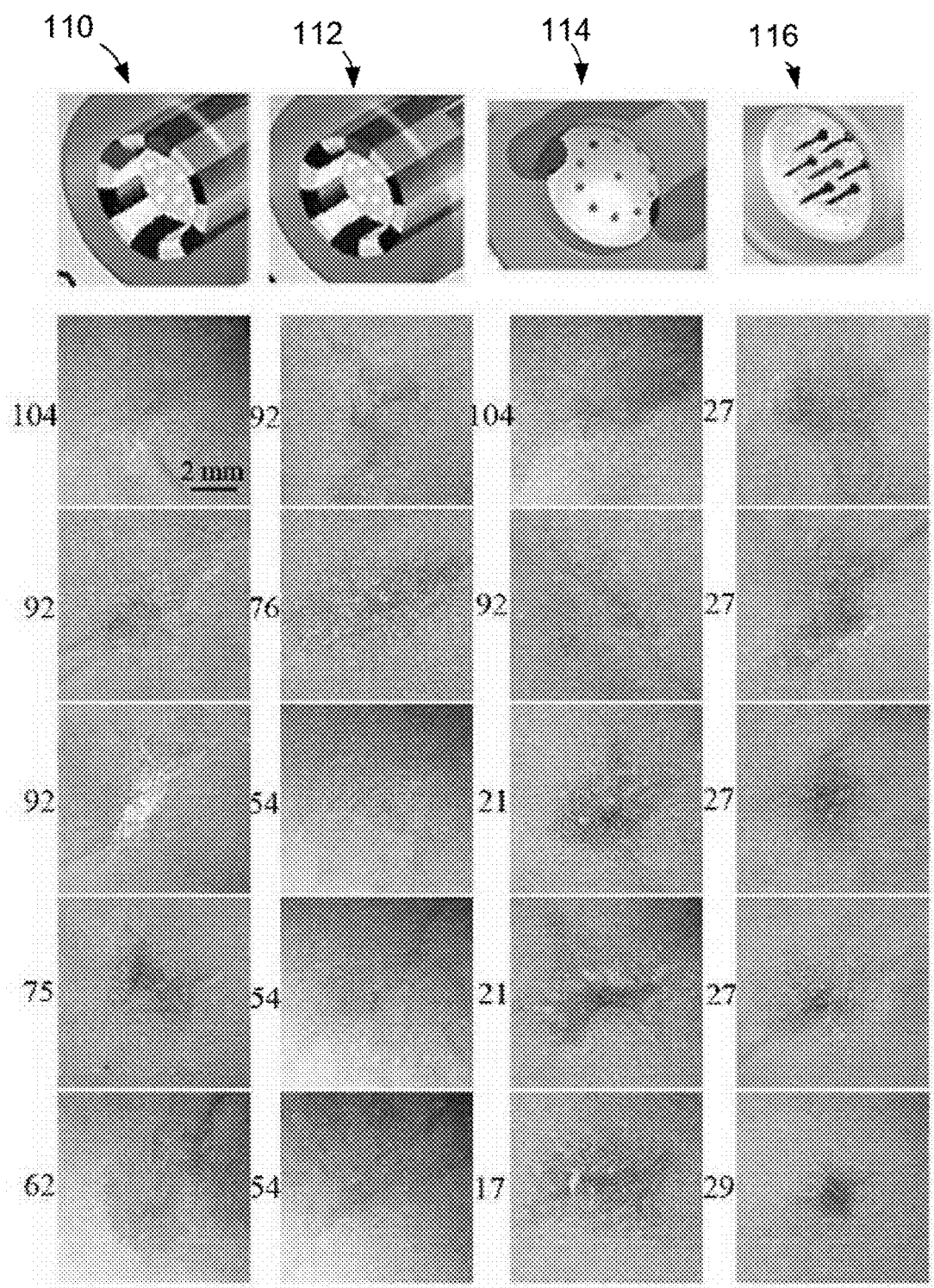
FIG. 25 shows a chart recording the reflected light images of different nsPEF-treated tumors for various electrode assembly configurations.

The appearance of nsPEF-treated skin on the indicated day following nsPEF therapy is shown in FIG. 25 in reflected light images of 20 different nsPEF-treated tumors. The electrode configuration 110, 112, 114, and 116 used is shown with respect to each column.

EXAMPLE 4

Figure 26:
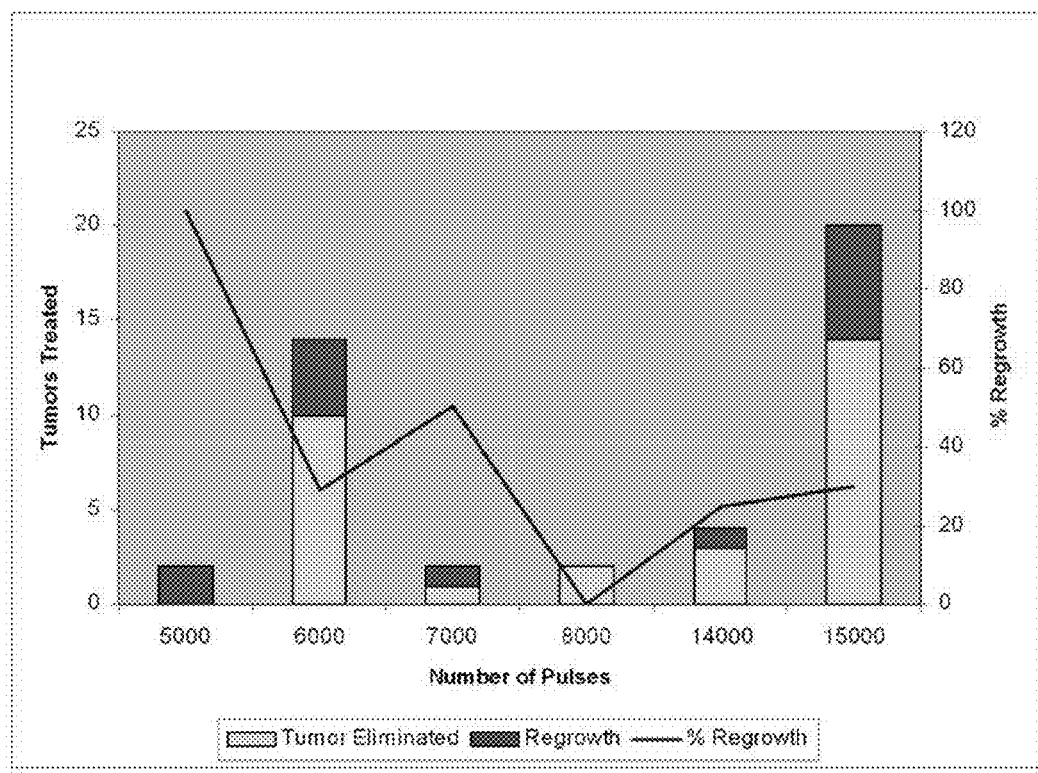
FIG. 26 shows a chart of number of tumors treated and the percentage of tumor regrowth recorded over the range of pulses applied during a single treatment for a pulse duration of 25 ns at 30 kV/cm and with 20-25 Hz pulse frequency.

A number of tumors were treated with nsPEF therapy over a range of pulses. With a pulse duration of 25 ns at 30 kV/cm and with 20-25 Hz pulse frequency, the number of tumors treated and the percentage of tumor regrowth were recorded over the range of pulses applied during a single treatment, as shown in the chart of FIG. 26. The chart illustrates how tumor elimination may be effected when at least 15,000 pulses were applied. Although the percentage of tumors eliminated was less than 100% at 15,000 pulses, complete tumor regrowth elimination may be potentially effected by treatment at a greater number of pulses when applied at these particular parameters.

Figure 27:
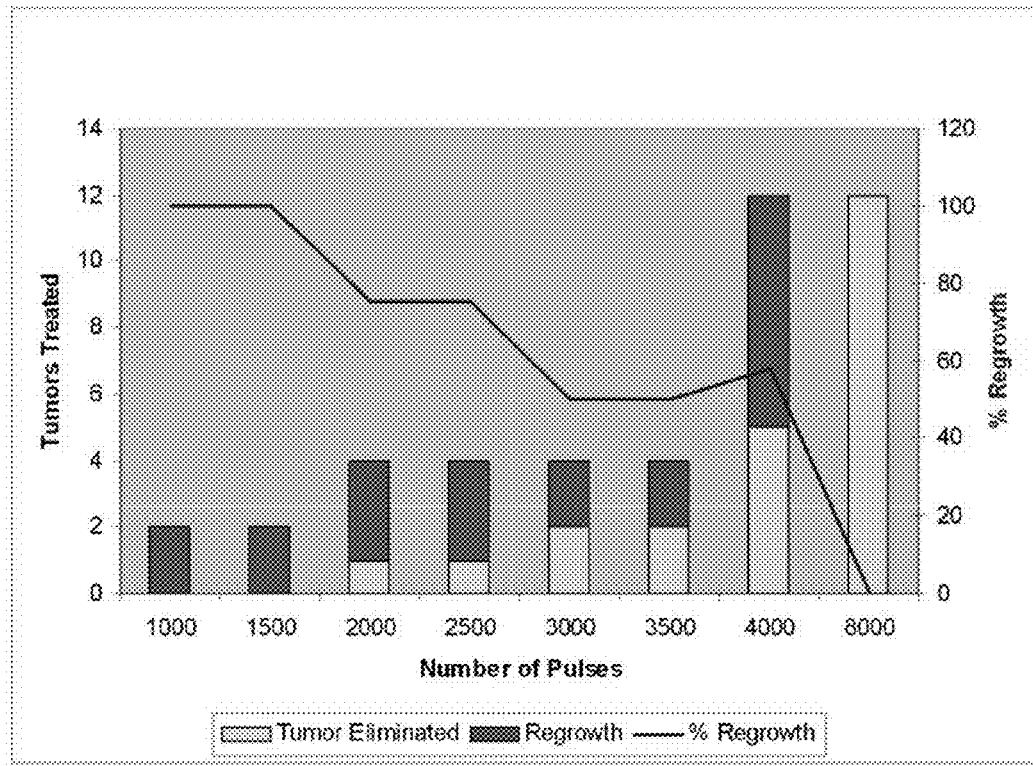
FIG. 27 shows a chart of number of tumors treated and the percentage of tumor regrowth recorded over the range of pulses applied during a single treatment for a pulse duration of 50 ns at 30 kV/cm and a pulse frequency of 20 Hz.

FIG. 27 likewise illustrates the number of tumors treated and the percentage of tumor regrowth over the number of pulses applied. As shown, with a pulse duration of 50 ns at 30 kV/cm and a pulse frequency of 20 Hz, the optimal pulse number applied for a single treatment may completely eliminate tumor regrowth at 8000 pulses. With these particular parameters, a number greater than 8000 pulses may also be potentially applied to effectuate complete tumor elimination.

The applications of the devices and methods discussed above are not limited to treatment of melanoma tumors but may include any number of further treatment applications. Moreover, such devices and methods may be applied to other treatment sites within the body. Modification of the above-described assemblies and methods for carrying out the invention, combinations between different variations as practicable, and variations of aspects of the invention that are obvious to those of skill in the art are intended to be within the scope of the claims.

What is claimed is:

1. A method for treating a tumor along a tissue region, comprising:
    positioning an electrode assembly in proximity to the tumor to be treated; and
    applying a nanosecond pulsed electric field to the tumor such that the tumor is necrosed after a single application of the field, where a temperature generated by the pulsed electric field in the tumor is no greater than 40° C.

2. The method of claim 1 wherein applying a nanosecond pulsed electric field comprises applying a pulse length of 50-900 ns.

3. The method of claim 1 wherein applying a nanosecond pulsed electric field comprises applying a pulse amplitude of at least 20 kV/cm.

4. The method of claim 1 wherein applying a nanosecond pulsed electric field comprises applying a pulse frequency of up to 7 Hz.

5. The method of claim 1 wherein applying a nanosecond pulsed electric field comprises applying a treatment time of up to 5 minutes.

6. The method of claim 1 wherein positioning an electrode assembly comprises applying a suction to the tissue region such that the tumor to be treated is positioned in apposition to the electrode assembly.

7. The method of claim 1 wherein applying a nanosecond pulsed electric field comprises passing electrically energy between at least one pair of apposed electrodes such that the energy passes through the tumor.

8. A method for treating a tumor along a tissue region, comprising:

positioning an electrode assembly in proximity to the tumor to be treated;

applying a nanosecond pulsed electric field to the tumor such that the tumor is eliminated after a single application of the field, wherein a temperature generated by the pulsed electric field in the tumor is no greater than 40° C.

wherein a pulse length ranges from 50-900 ns, and wherein a pulse amplitude ranges from at least 20 kV/cm.

9. The method of claim 8 wherein applying a nanosecond pulsed electric field comprises applying a treatment time of up to 5 minutes.

10. The method of claim 8 wherein positioning an electrode assembly comprises applying a suction to the tissue region such that the tumor to be treated is positioned in apposition to the electrode assembly.

11. The method of claim 8 wherein the pulse length ranges from 100-300 ns.

12. The method of claim 8 wherein the pulse amplitude ranges from 20 kV/cm to 30 kV/cm.

13. The method of claim 8 wherein the pulse frequency ranges up to 7 Hz.

* * * * *